US006953456B2

(12) United States Patent
Fuchs et al.

(10) Patent No.: US 6,953,456 B2
(45) Date of Patent: Oct. 11, 2005

(54) TAMPON HAVING AN OVAL FORM AFTER EXPANSION AND PROCESS FOR PRODUCING THE SAME

(75) Inventors: Sybille Fuchs, Frankfurt am Main (DE); Samantha Jane Price, Twickenham (GB); Uwe Thomas Michael Horst Hirsch, Griesheim (DE); Veronique Marie Josephine Kremer, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 280 days.

(21) Appl. No.: 10/149,877

(22) PCT Filed: Dec. 8, 2000

(86) PCT No.: PCT/US00/33208

§ 371 (c)(1), (2), (4) Date: Oct. 3, 2002

(87) PCT Pub. No.: WO01/43680

PCT Pub. Date: Jun. 21, 2001

(65) Prior Publication Data

US 2003/0208180 A1 Nov. 6, 2003

(51) Int. Cl.[7] ........................... A61F 5/44; A61F 13/20; A61F 13/15

(52) U.S. Cl. ....................... 604/904; 604/330; 604/354; 604/379; 604/385.17

(58) Field of Search ................................ 604/904, 354, 604/330, 328, 379, 385.17, 385.18

(56) References Cited

U.S. PATENT DOCUMENTS

| | | | | |
|---|---|---|---|---|
| 3,068,867 A | | 12/1962 | Bletzinger | |
| 3,674,030 A | | 7/1972 | Jones | |
| 3,710,420 A | | 1/1973 | Yamauchi | |
| 3,726,277 A | * | 4/1973 | Hirschman | 604/359 |
| 4,816,100 A | * | 3/1989 | Friese | 156/191 |
| 6,358,235 B1 | * | 3/2002 | Osborn et al. | 604/385.18 |
| 6,758,839 B2 | * | 7/2004 | Lochte et al. | 604/385.18 |
| 2002/0107497 A1 | * | 8/2002 | Osborn et al. | 604/385.18 |
| 2003/0208179 A1 | * | 11/2003 | Fuchs et al. | 604/385.17 |

FOREIGN PATENT DOCUMENTS

| | | | | |
|---|---|---|---|---|
| DE | 1815541 | | 7/1970 | |
| DE | 200 02 337 U1 | * | 4/2000 | A61F/13/20 |
| EP | 0 546 256 A1 | | 6/1993 | |
| WO | WO 94/15564 A1 | | 7/1994 | |
| WO | WO 97/23185 A1 | | 7/1997 | |

* cited by examiner

*Primary Examiner*—Larry I. Schwartz
*Assistant Examiner*—Michael G. Bogart
(74) *Attorney, Agent, or Firm*—Ingrid N. Hickman

(57) ABSTRACT

Digital tampons are disclosed which are capable of radially expanding into a non circular cross-sectional shape upon exposure to a wet environment, typically in use condition, so as to reduce bypass leakage. The inventions also relates to tampon blanks and a process of producing the tampons.

13 Claims, 14 Drawing Sheets

I 6 12 I 5
5
1
X 2
5
3
1
X
2
5
3

1
2
3
4
6
X

Fig. 10
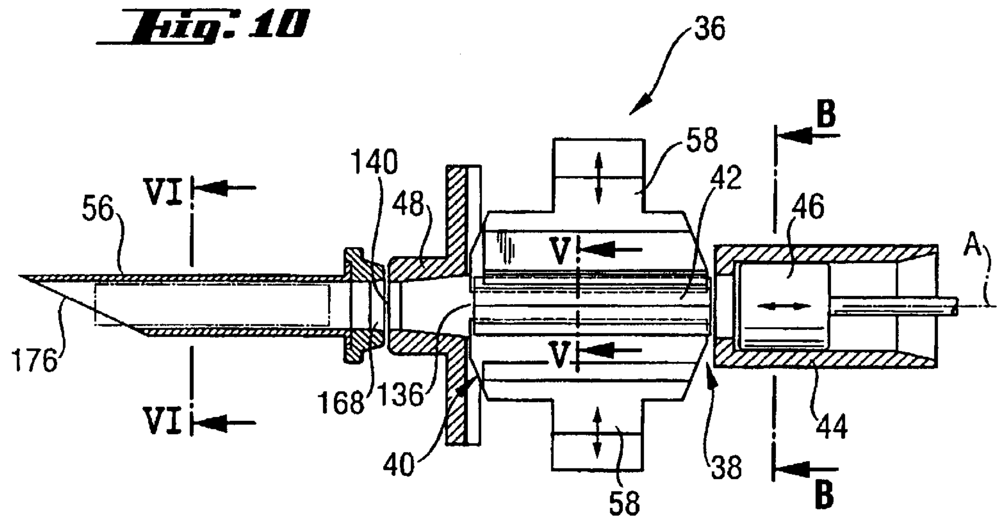
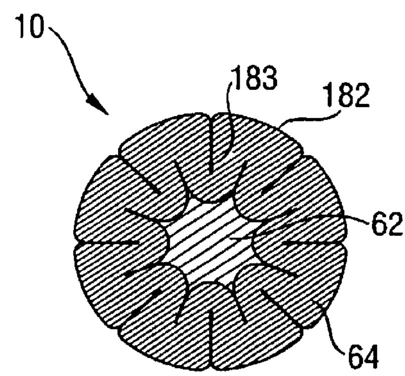
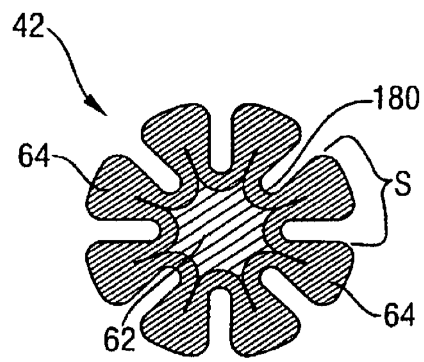
Fig. 12
Fig. 11

[1] min 100 mm long; (1,5 +/- 0,15) mm I.D.

[2] see 5.2.2

[3] see 5.2.3

Top View

[1]MATERIAL: Glass or transparent plastic.

TAMPON HAVING AN OVAL FORM AFTER EXPANSION AND PROCESS FOR PRODUCING THE SAME

CROSS REFERENCE TO RELATED APPLICATION

This application claims benefit of the National Stage of International Application No. PCT/US00/33208, filed Dec. 8, 2000; and EPO 99124778.4, filed Dec. 14, 1999.

FIELD OF THE INVENTION

The present invention relates to compressed, radially-expanding fibrous digital tampons for vaginal use as well as to a process of making the same. These digital tampons expand into a non-circular shape upon exposure to a wet environment, typically upon exposure to vaginal/menstrual fluids during use.

BACKGROUND OF THE INVENTION

Generally vaginal tampons are manufactured from absorbent fibers, such as rayon, cotton, or a mixture of both fibers. In the case of digital tampons (i.e., tampons without any applicator aid) the volume of absorbent fibers necessary, to provide sufficient absorption capacity must be highly compressed to form a substantially circular tampon of sufficiently small size to allow comfortable insertion into the body. The compression must be adequate to provide the tampon with axial stability such that the circular shape is maintained until the insertion is completed. Such compression for digital vaginal tampons is typically provided as radial compression. As a result the tampon when first inserted into the body is often compressed into a relatively non-conformable form with a relatively high initial density.

A drawback associated with such digital tampons (which are currently commercially available) is that they are not able to appropriately conform to the vaginal walls after insertion. Thus menstrual fluid may flow along the tampon's side and bypass its absorbent portions. Thus such tampons are susceptible to bypass leakage.

There have been attempts to address the problem of early bypass leakage. For example WO 97/23185 discloses the use of appropriate fibre mixtures providing rapid expansion properties to a compressed tampon, like mixtures of non-limbed fibres together with multi-limbed regenerated cellulose fibers.

However, consumer needs have not been fully satisfied. There is still a need of providing digital tampons that would reduce or even prevent bypass leakage (early on and during use) while delivering effective absorption capacity.

It is a further object of the present invention to provide a digital vaginal tampon having substantial dimensional stability prior use and thus being easy to insert by digital application while exhibiting improved expansion characteristics in a wet environment (typically in use conditions).

The present invention achieves these objects by means of the features contained in the claims. It has now surprisingly been found that a digital vaginal tampon made of a cylindrical mass of compressed fibers and having the ability of radially expanding in a non-circular shape, preferably an ellipsoidal shape, upon exposure to a wet environment, provides a better adaptation to the non-circular morphology of the vagina thereby reducing bypass leakage while exhibiting effective absorption capacity.

Advantageously the tampons herein when flared by the user before digital insertion in the vagina have the tendency to take an ellipsoidal shape at the withdrawal flared end, thereby facilitating finger grip for digital insertion.

SUMMARY OF THE INVENTION

The present invention encompasses a digital tampon for feminine hygiene or medical purposes comprising a substantially cylindrical mass of compressed fibers, the tampon being capable of radially expanding into a non-circular shape upon exposure to a wet environment, so that the ovality coefficient of the tampon measured at the end point of the EDANA syngina method, referred to as OC (expanded tampon), is higher than 10.

The present invention also relates to a tampon blank obtainable by winding essentially upon itself a portion of length of nonwoven material which has a width approximately corresponding to the length of the tampon, preferably in presence of a fluid permeable covering material, so that the ovality coefficient of the tampon blank, referred to as OC(tampon blank), is higher than 10.

Finally the present invention also encompasses a process for producing a digital tampon according to the present invention in which a tampon blank as defined above is shaped by winding up a nonwoven material, preferably in presence of a fluid permeable covering material, the tampon blank is then pressed radially to form a tampon preform which has a central approximately cylindrical fibre core and longitudinal ribs which extend radially outwards from the fiber core. In the preferred embodiment the tampon blank is pressed radially relative to a longitudinal axis, which axis is offset from the mid-axis of the tampon blank. This radial compression is such that the resulting preform is then allowed to expand into its final shape, preferably inside a cylindrical pipe, so that the outer surface of the tampon forms a soft cylindrical surface of at least slightly bigger diameter than the tampon preform.

BRIEF DESCRIPTION OF THE DRAWINGS

The invention is explained in more detail below by means of the diagrammatic drawings of an exemplary embodiments of the tampon, the tampon blank and of a process for their production with reference to apparatus illustrated schematically in the drawings, in which:

FIG. 10 shows an apparatus for producing the tampon according to FIG. 9 in a longitudinal section FIG. 11 shows a cross-section through a pressed tampon preform along line V—V in FIG. 10

FIG. 12 shows a cross-section through a ready-pressed tampon along line VI—VI in FIG. 10

DETAILED DESCRIPTION OF THE INVENTION

The digital vaginal tampons of the present invention comprises a substantially cylindrical mass of compressed fibers, said tampons having the ability to radially expand in a non-circular cross-sectional shape, preferably an ellipsoidal shape, upon exposure to a wet environment, typically upon contact with menstrual discharge during use. In a preferred embodiment herein the tampons have a substantially circular cross-section (before vaginal use) but are capable of radially expanding into a non-circular cross-sectional shape upon exposure to a wet environment (during vaginal use). This property has the advantage in use that the tampon radially expands more adequately to conform with the vaginal morphology of a women which is rather a flattened cavity than a circular cavity. The present invention also relates to tampon blanks and to a process of manufacturing the tampons of the present invention.

As used herein the term 'radially expand' relates to the expansion of the tampons herein in use conditions. These tampons expand primarily in a direction perpendicular to the central axis of the tampon. According to the present invention the tampons expand non-uniformly in at least two directions perpendicular to the central axis (herein called minor and major diameter). Preferably the tampons herein expand non-uniformly in all directions perpendicular to the central axis so as to be elliptically shaped upon exposure in a wet environment.

Figure 6:
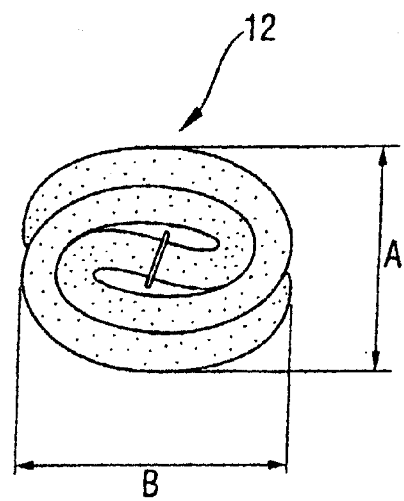
FIG. 6 shows a cross-section view of a tampon blank of FIG. 5, taken along line I—I.

According to the present invention the tampon blank, the tampon and expanded tampon (typically the tampon during use condition) can be defined as having a central axis, a minor diameter and a major diameter, the major diameter of the tampon blank/tampon/expanded tampon being measured perpendicular to said central axis at an angle of 90° from the minor diameter. This is for example illustrated in FIG. 6 for the tampon blank, where the minor diameter stands for A and the major diameter for B.

According to the present invention the minor diameter is defined as the narrowest diameter of respectively the tampon blank or tampon/expanded tampon. The minor diameter will be suitably measured with the use of a Tampon Gauge with a calliper that is accurate to 0.1 mm. A suitable tampon gauge for use herein is Mitutuyo Digimatic Scale Unit #572-213, 0–300 mm. According to the present invention once the minor diameter is identified the tampon/expanded tampon or tampon blank is turned at an angle of 90° to measure the major diameter, which typically corresponds to the widest diameter of respectively the tampon/expanded tampon or tampon blank.

The minor and major diameters considered herein are the ones taken on a given cross section of respectively the tampon blank, tampon or expanded tampon. Thus the diameters considered can be taken on the top, middle or bottom or any other positions on the tampon core (as opposed to the head which preferably further undergoes the formation of the elongated insertion end) provided that the diameters on the same position are compared to each other. For the tampon blank these measurements can be taken at any position of its length provided the minor and major diameters on a same position are compared to each other.

Based on these measurements an ovality coefficient referred to as OC which is a measure of the cross-sectional shape can be defined for respectively the tampon blank, tampon and expanded tampon, as defined by the following equation $$\frac{\text{Major diameter} - \text{minor diameter}}{\text{Minor diameter}} * 100$$

According to the present invention the tampons herein are defined by their ovality coefficient measured at the end point of the Edana syngina method, herein referred to as OC (expanded tampon). For the tampons herein the OC (expanded tampon) is of more than 10, preferably more than 13, more preferably from 15 to 40, more preferably from 16 to 35, even more preferably from 18 to 30 and most preferably from 20 to 28.

The 'end point' of the EDANA syngina method is defined by the first drop of syngina fluid that exits the syngina apparatus when following the EDANA syngina method.

Standard Syngyna Test

1. Scope

This standard method specifies a test procedure for the in-vitro measurement of absorbency of menstrual tampons by the Syngina method. It is a quality control test that is used in production sites for:

a) determining conformance to internal manufacturing specifications, and b) for ensuring compliance to the EDANA Code of Practice for Tampon Labeling that has been agreed with the European Commission. It is important to note that this laboratory test is not intended to be used for predicting absorbency in vivo.

The protocol has been used by the tampon industry globally for more than 30 years and it is favored by some regulatory authorities. It is applicable for products with an absorbency of up to 25 grams. The coefficient of repeatability has been estimated for an absorbency of around 10.5 grams to be less than 5%.

2. Normative References

The following standards contain provisions which, through reference in this text, constitute provisions of this standard method. For dated references, subsequent amendments to, or revisions of, any of these publications do not apply. However parties to agreements based on this standard method are encouraged to investigate the possibility of applying the most recent editions of the standards indicated below. For undated references, the latest edition of the standard referred to applies.

5725, Precision of test methods

ASTM 3492-83, Standard Specification for Rubber Contraceptives (Condoms)

ASTM D 3492-97, Standard Specification for Rubber Contraceptives (Male condoms)

3. Terms and Definitions

For the purposes of this standard method the following definitions apply:

3.1 Syngina

The term is derived from "Synthetic vagina".

3.2 Menstrual tampon/tampon

A device to be inserted into the vagina to absorb menses.

4. Principle

The principle is to simulate the vaginal environment in the laboratory by applying standard pressure to a tampon inside a flexible membrane (a certain type of condom) and then introducing defined amounts of fluid until the tampon leaks. The tampon weight is taken before and after the test to calculate the weight of fluid absorbed.

5. Apparatus 5.1 Standard laboratory equipment 5.2 Syngina apparatus

Figure 23:
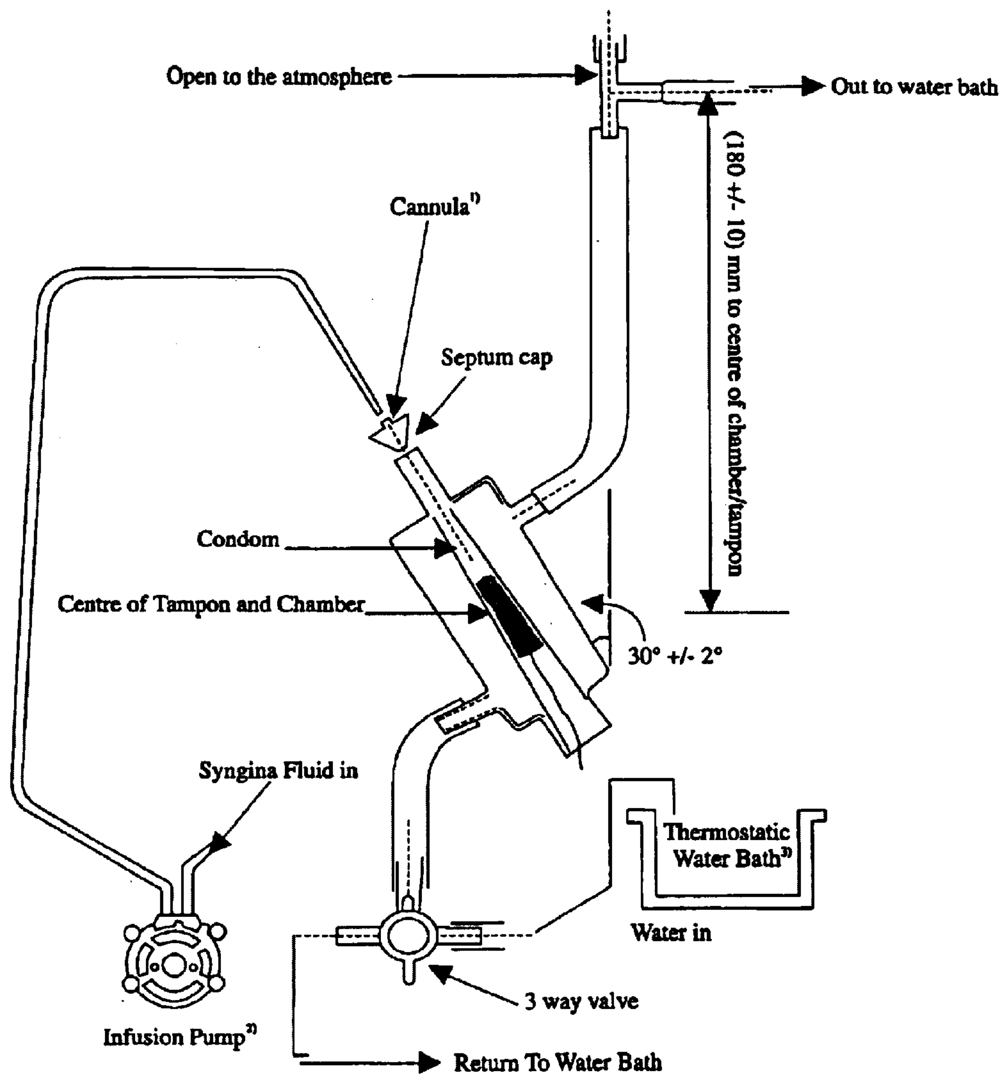
FIG. 23 shows the syngina apparatus of the EDANA tampon absorbency method.

The Syngina apparatus set-up is illustrated in FIG. 23. This is designed to provide constant hydrostatic pressure of (180±10) mm.

Figure 24:
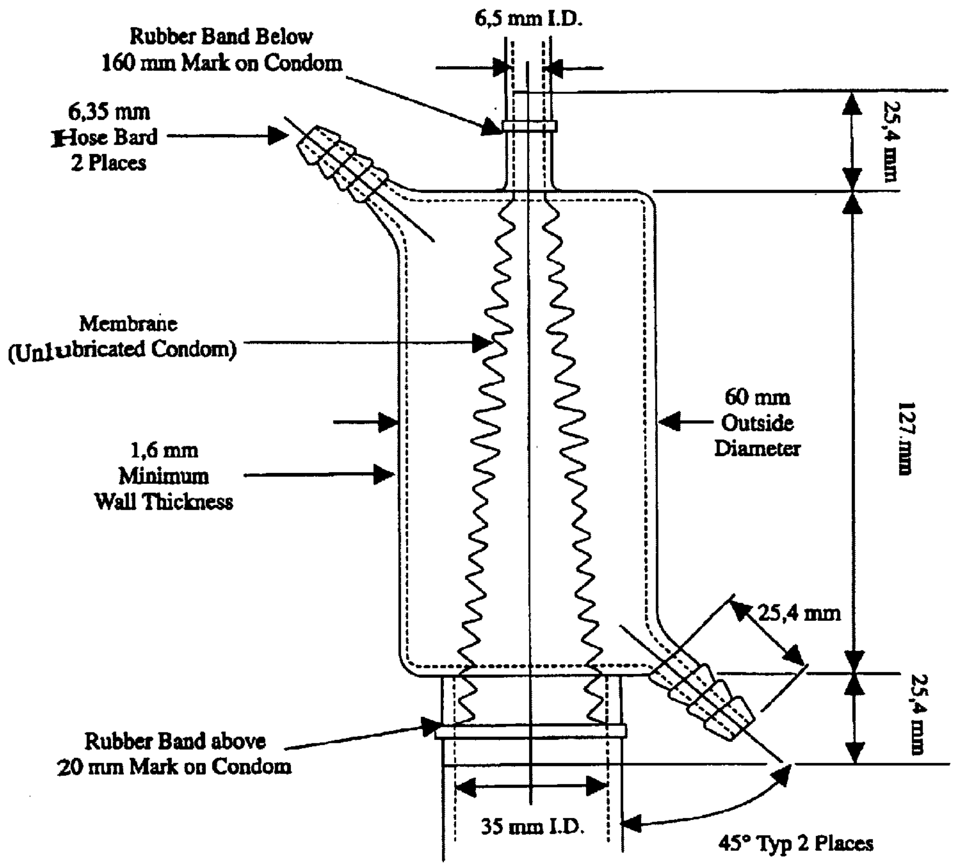
FIG. 24 shows the syngina chamber of the EDANA tampon absorbency method.
Figure 24:
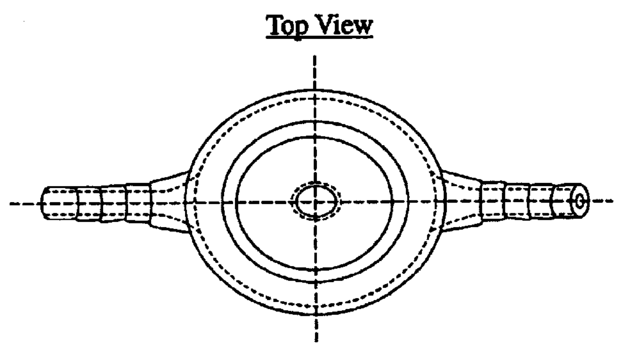

5.2.1 Syngina chamber, details of which are provided in FIG. 24.

5.2.2 Infusion pump, set up to deliver (50±2) ml/hour.

5.2.3 Thermostatic bath, with external circuit, set up to (27±1)° C.

5.3 Straight unlubricated condoms having a tensile strength between 17 MPa and 30 MPa measured in accordance with ASTM D 3492-83 and ASTM D 3492-97. Note: For condom installation and replacement: see Section 10.

6. Reagents

Syngina fluid

The formulation and preparation are given below:

Distilled or de-ionised water.

Sodium chloride (analytical reagent grade).

Color agent: acid fuchsin, Fisher F97 Certified Biological Stain, Color Index No 42685; Fisher Scientific Company or Fruchterot dye, E 144 or Ponceau Cochenillerot E 124 or FD&C Red #40.

Sodium chloride solution: Dissolve 10 grams sodium chloride in 1 liter distilled or de-ionised water.

Syngina fluid: Dissolve 0.5 gram color agent in 1 liter sodium chloride solution.

Syngina fluid should be regularly replaced to avoid microbiological contamination.

Syngina fluid should be stored and used at room temperature.

7. Preparation of Test Specimens 7.1 The test specimen (tampon) shall be removed from its wrapping and applicator, if applicable.

7.2 The test specimen shall be unwrapped immediately before testing.

7.3 The number of specimens per test, and sampling instructions, must be defined for each specific application.

8. Procedure 8.1 Weigh the tampon to be tested (including withdrawal cord) to the nearest 0.01 gram. Record the weight.

8.2 With the Syngina chamber empty, place the tampon within the condom so that the center of the tampon is at the center of the chamber and the withdrawal cord is positioned toward the bottom of the chamber. See FIG. 23.

8.3 Insert the infusion needle (cannula) through the optional septum cap so that it contacts the top end of the tampon.

8.4 Fill the outer part of the chamber with water and adjust the flow such that water trickles over the head and back to the water bath. The liquid must not rise into the atmospheric vent. Examine the position of the tampon and, if necessary, drain, re-center and repeat steps 8.3 and 8.4.

8.5 Pump the Syngina fluid into the chamber.

8.6 The "end point" is defined by the first drop of liquid that exits the apparatus. Terminate the test by stopping the fluid flow. Note: The test shall be discarded if fluid is detected in the folds of the condom before the tampon is saturated.

8.7 Drain the water from the chamber, remove the tampon and weigh it immediately to the nearest 0.01 gram. Record the wet weight.

8.8 After the tampon has been weighed, carefully remove any residual fluid (with non-fiber shedding absorbent laboratory wipes) from the inside of each condom in preparation for the next test. Note: If the test stand comprises more than one chamber, use tampons with the same absorbency, for parallel testing.

9. Calculation and Expression of Results 9.1 Calculate the absorbency of each specimen tampon as follows:

A=B−C where: A=Absorbency of tampon in grams

B=Weight in grams of saturated tampon

C=Weight of dry tampon in grams and express the results to the first decimal.

9.2 Calculate the average absorbency of the total number of test specimens.

Figure 22:
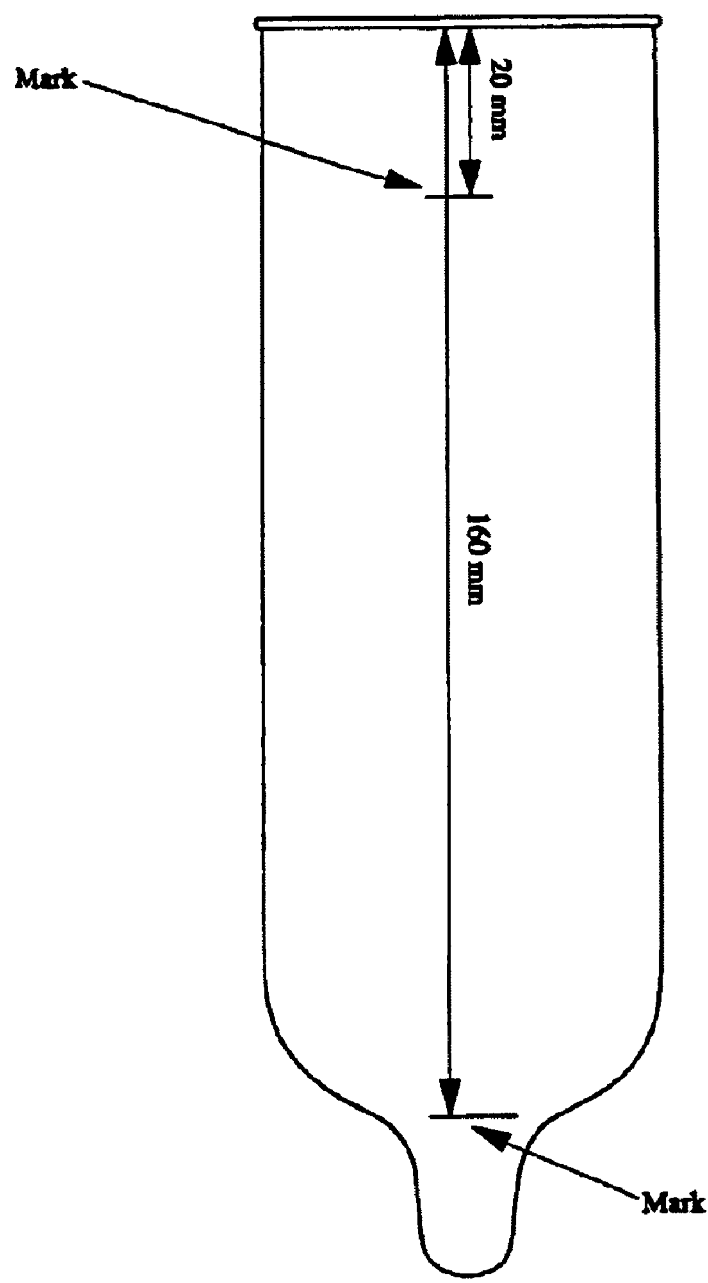
FIG. 22 shows the condom marking of the EDANA tampon absorbency method.

10. Condom Installation and Replacement Instruction a. Open and unravel a condom.

b. Mark the condom at 20 mm and 160 mm length from the open end (see FIG. 22).

c. Insert the condom through the chamber with the aid of a rod so that the 160 mm mark rests on the edge of the smaller opening of the chamber (see FIG. 24).

d. Cut the tip of the condom and secure with a rubber band, such that the 160 mm mark remains on the edge of the small opening of the chamber.

e. Draw the condom through the large chamber opening so that the 20 mm mark rests on the opening's edge (see FIG. 24) and secure with a rubber band.

f Replace condoms (a) if they leak, (b) after every tenth test or (c) daily—whichever applies first.

It has now been found that the tampons according to the present invention having the radial expansion characteristics as described herein when exposed to a wet environment have the ability to reduce or even prevent bypass leakage. By 'bypass leakage' is meant the phenomenon in which menstruation fluid can escape between the body walls and the tampon. Indeed the tampons herein have the ability in use to radially expand in a non-circular shape, preferably an ellipsoidal shape, i.e., a radial expansion which more adequately conform to the vagina anatomy and therefore helps reducing bypass leakage or even prevent it. Also the surface area of the circumference of a non-circular (e.g., ellipsoidal shape) expanded tampon according to the present invention upon exposure to a wet environment is bigger than those of a similar tampon (i.e., a tampon having same fiber weight, bulk density (weight of tampon per volume) and stability) that radially expands in a circular cross-sectional shape (as opposed to non circular) upon exposure to the same wet condition. This results in enhanced vaginal fluid capture at the circumference of the tampon and faster fluid absorption in use. The increased surface area at the circumference of the tampon is evidence of a better utilisation of the absorbency of the fiber material per unit weight.

The tampons herein comprise a substantially cylindrical mass of compressed fibers. The tampons herein are made from nonwoven material/fibers which may be made of natural fibres such as cotton, wood pulp, jute and the like and/or processed fibres as regenerated cellulose, cellulose nitrate, cellulose acetate, rayon, polyester, polyvinyl alcohol, polyolefin, polyamine, polyamide, polyacrylonitrile, and the like. Other fibres in addition to the above fibres may be included to add desirable characteristics to the digital tampons. Preferably the tampon fibres are rayon or cotton and more preferably rayon. The fibres may have any useful cross-section. Preferred cross-sections include multi-limbed and non-limbed. Multi-limbed, regenerated cellulosic fibres have been commercially available for a number of years. These fibres are known to possess increased specific absorbency over non-limbed fibres. One commercial example of these fibres is the Galaxy® viscose rayon fibres available from Acordis England. These fibres are described in details in Courtaulds European application EP-A-1301874, the disclosure of which is herein incorporated by reference. These multi-limbed fibres are described as comprising a solid filament of regenerated cellulosic material having a decitex of less than 5.0 and multi-limbed cross-section, each limb having a length to width ratio of at least 2:1. The fibres are preferably staple length fibres having three or four limbs and a generally symmetrical cross-sectional shape, e.g., Y-, X, H, or T-shaped. A preferred cross-sectional shape is Y-shaped having an angle between limbs of about 120. Preferred regenerated cellulosic materials are viscose having a cellulose content of 5% to 12% and a caustic soda content of 4% to 10%. The fibres are preferably spun having a salt figure of 4.0 to 12.0.

Preferably the tampons herein include from 20% to 100% of multi-limbed fibres. Indeed these multi-limbed fibres are believed to accelerate the radial expansion properties of the tampons herein upon exposure to a wet environment and thus contribute to the benefit of the present invention by further reducing the occurrence of early bypass leakage. The fibres may be a mixture of multi-limbed fibres and non-limbed fibres. Preferably the tampons herein include from 20% to 100% of multi-limbed fibres and from 80% to 0% of the non-limbed fibers. More preferably the tampons herein include from 25% to 100% of multi-limbed fibres and from 75% to 0% of the non-limbed fibers. What ever the fibers used herein or mixtures of fibers used herein they are preferably blended to a substantially uniform mixture of fibers. These fiber blending operations are known to those skilled in the art. For example, the fibers can be continuously metered into a saw-tooth opener. The blended fibers can be transported, e.g., by air through a conduit a carding station to form a fibrous nonwoven material/web. This nonwoven material is then further processed as mentioned herein to form the tampon. In the tampon forming process the web/material is formed into a narrow, fibrous sliver and spirally wound to form the tampon blank. In addition a liquid permeable covering material is preferably wrapped around the tampon blank to substantially contain the fibrous absorbent portion of the tampon.

Useful covering materials are those known to those skilled in the art. They may be selected from an outer layer of fibers which are fused together (such as by thermobonding), a nonwoven fabric, an apertured film or the like. Preferably the covering material has a hydrophobic finish. Suitable materials for use herein include polyester/polyethylene bicomponent structure and polyethylene-sulfonic acid/polyethylene bicomponent structure.

Figure 1:
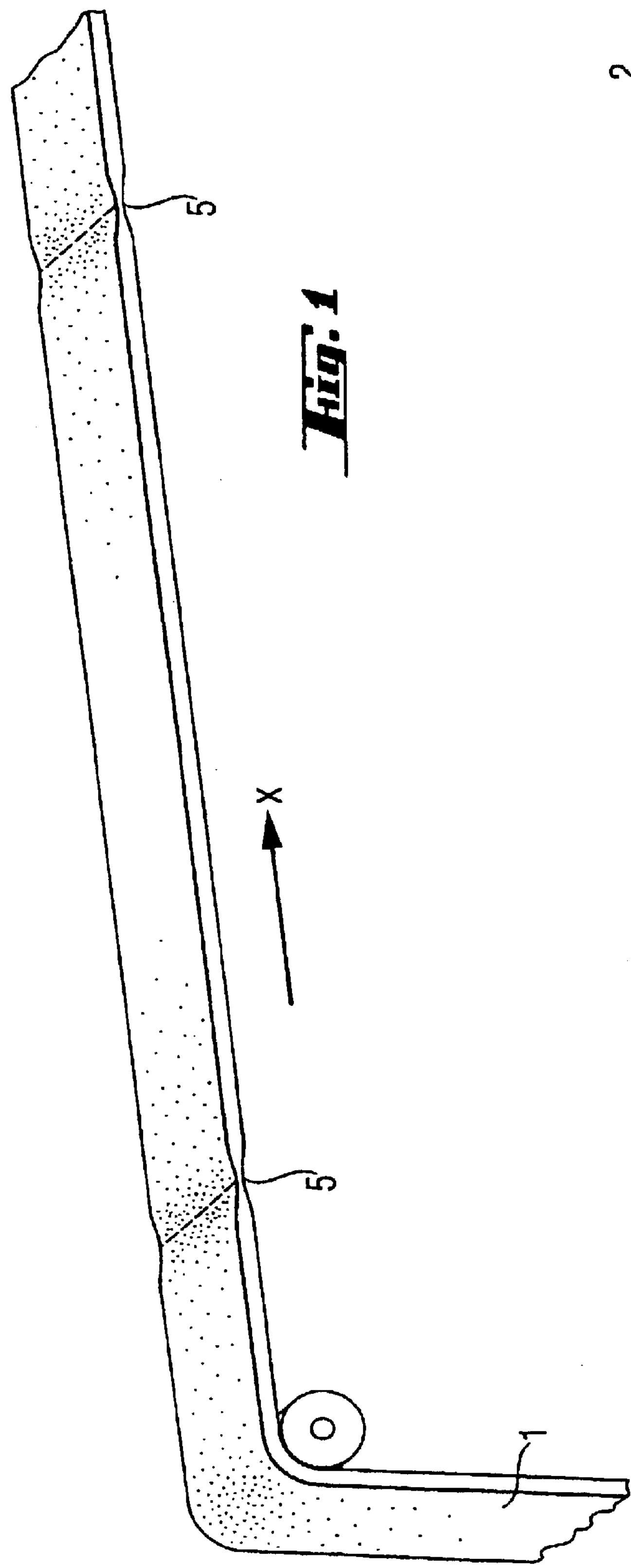
FIG. 1 to FIG. 4 show steps for producing a tampon blank according to the present invention
Figure 2:
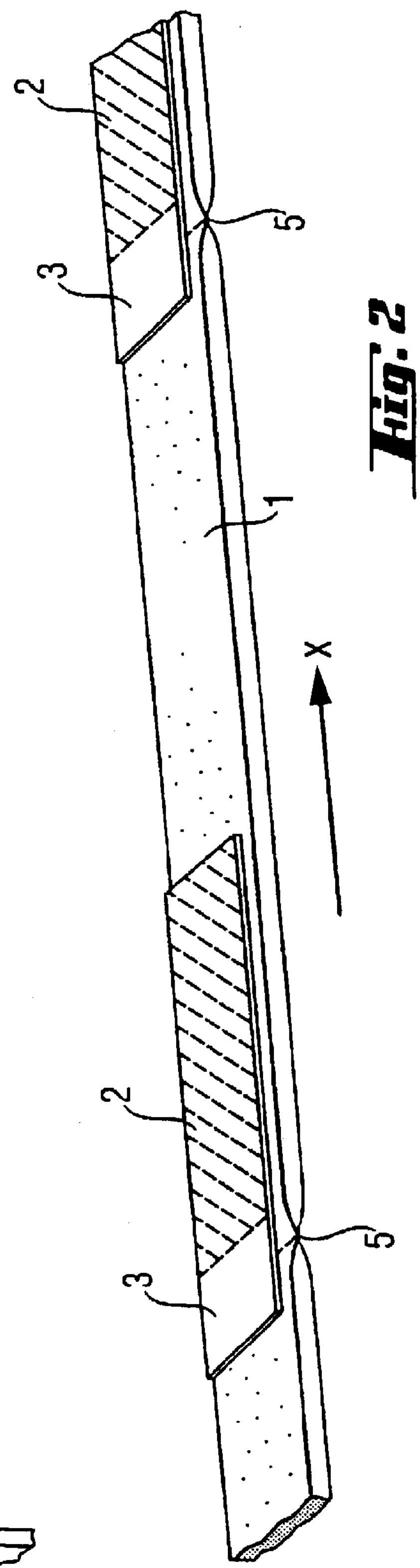
Figure 9:
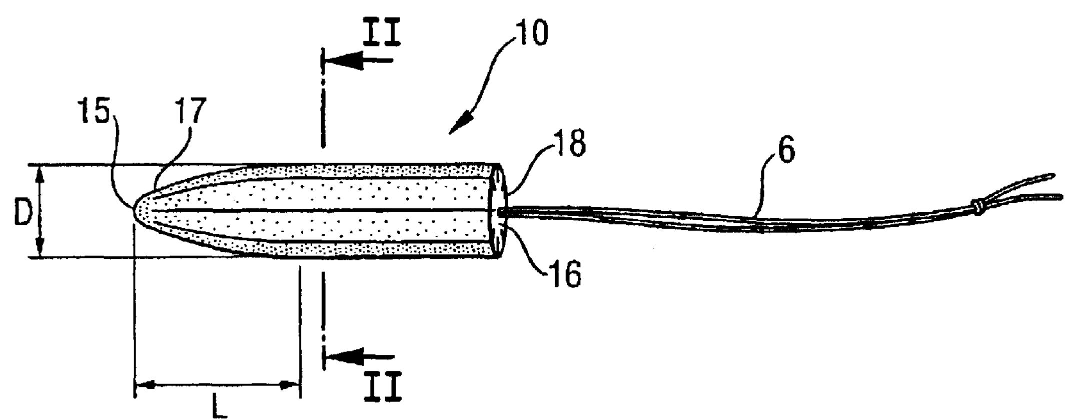
FIG. 9 shows a perspective view of a tampon according to the present invention
Figure 9A:
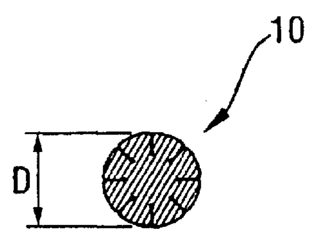
FIG. 9*a* shows a cross-section view of a tampon of FIG. 9, taken along line II—II

FIG. 9 shows a tampon 10 for feminine hygiene formed from a tampon blank 12 which is shaped by winding up a nonwoven material 1, preferably in presence of a fluid permeable covering material 2. Indeed in a preferred embodiment herein the tampon comprises a fluid-permeable covering material 2 such that the cylindrical mass of compressed fibers is substantially enclosed by the covering material. According to FIG. 2 a covering material 2 which is a nonwoven covering material which is at least partly composed of thermoplastic material is sealed onto the part of the nonwoven material 1 which forms the circumferential surface of the tampon 10, using heat and pressure, the fluid covering material 2 being preferably longer than the circumference of the tampon blank 12. Typically the thermoplastic non-woven covering material 2 is connected to the nonwoven material 1 by means of parallel weld lines at various distance from one another. Other attachment patterns may be used, such as discontinued dots, etc.

A preferred process for producing the tampon blank herein is illustrated in FIGS. 1 to 4. According to FIG. 1 a calendered nonwoven material, which typically consists of a mixture of natural or cellulosic fibres and which has a width corresponding to the length of the tampon 10, is fed continuously. The nonwoven material is weakened transversely to its longitudinal direction in each case by so-called weak points 5, for example by being perforated, between sections of length which are needed for the production of the tampon 10. Approximately at the same time, a continuously fed fluid permeable covering material 2 (FIG. 2) is cut into a covering material section, whose length exceeds the circumference of the tampon blank 12. The covering material 2 is then fastened, for example by sealing or needling, onto the outside of a region of the material 1 which is located at the rear in the direction of the movement x of the material 1 and in front of the weak points 5, with the exertion of heat and pressure. The arrangement of the covering material 2 on the upper side of the nonwoven material 1 is in this case provided such that the end 3 of the covering material 2 which is on the outside and the rear in the direction of movement x of the material 1 extends freely, that is to say without being sealed, beyond the weak points 5. The nonwoven material is then cut through the weak points to allow winding upon itself to form a tampon blank. The outer end 3 of the covering material 2 which extends beyond the outer end 4 of the nonwoven material 1, is welded, using heat and pressure, to the outside of a portion of the covering material 2.

Figure 5:
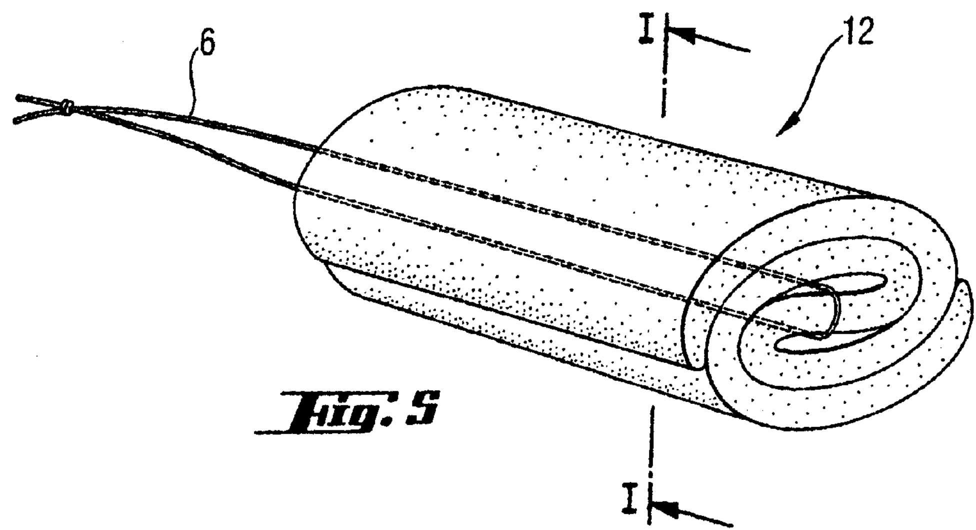
FIG. 5 shows a diagrammatic view of a tampon blank according to the present invention
Figure 7:
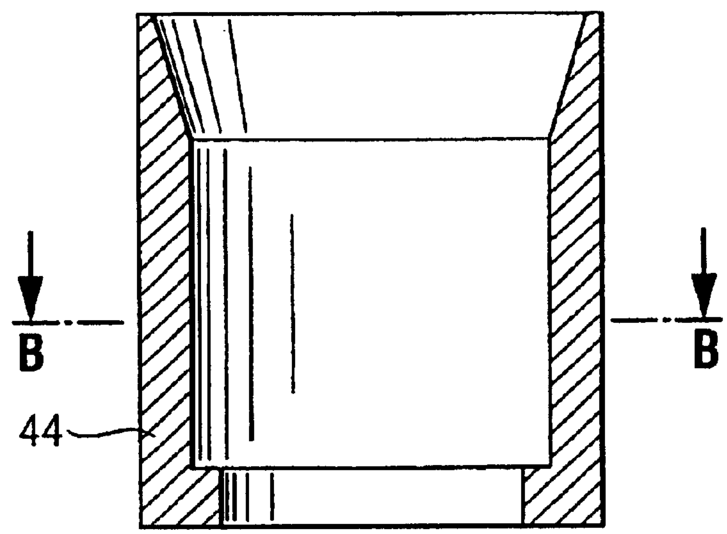
FIG. 7 shows a longitudinal mid-section view of the tube 44 disposed before the preforming press 36 (cf FIG. 10), this tube (also called arm) serves the function of transporting the tampon blank to the preforming press while shaping the tampon blank in a non-circular cross-sectional shape
Figure 8:
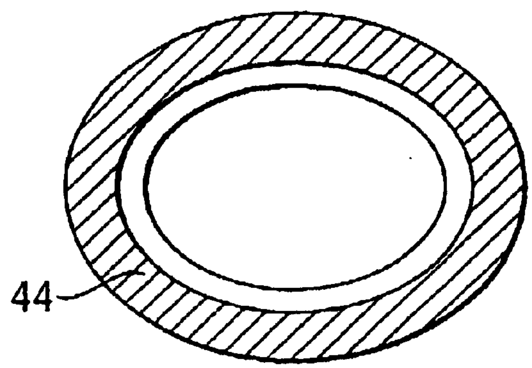
FIG. 8 shows an ellipsoidal cross section of the tube 44 taken along line B—B in FIG. 7 or 10

The tampon blank 12 according to the present invention has a non-circular cross-section along its entire length as defined hereinafter by the OC(tampon blank). This can be achieved by winding up the nonwoven material 1, preferably including the covering material 2 directly in a tube that has the desired non-circular cross-sectional shape or by winding up these materials in a circular-shaped tube and then transporting the resulting blank in another tube (see 44 in FIG. 10) having the desired non-circular cross-sectional shape, preferably an ellipsoidal shape. Such a tube 44 also called arm serves the function of transporting the tampon blank in the press while giving to the blank the desired non-circular cross-sectional shape. FIGS. 7 and 8 illustrate a preferred tube 44 for use herein, especially FIG. 8 illustrates the cross sectional ellipsoidal shape of tube 44. Reference is made to FIG. 5 which shows a tampon blank according to the present invention having been shaped by the tube 44 of FIG. 10, before entering the preforming press 36. The minor diameter is the one taken along line A and the major diameter is the one taken along line B see FIG. 6.

The resulting tampon blank before being pressed radially in the preforming press has an ovality coefficient according to equation defined herein:

$$\frac{\text{Major diameter} - \text{minor diameter}}{\text{minor diameter}} * 100,$$

referred to as OC (tampon blank) of more than 10, preferably more than 15, more preferably from 18 to 45, more preferably from 20 to 40 and most preferably from 22 to 35.

It has now surprisingly been found that by producing a tampon starting from a tampon blank with a non-circular cross section as opposed to a circular one before radial compression, the resulting tampon has the improved expansion characteristic described herein before. Indeed the tampon blanks as described herein as well as the process of producing tampons as described herein are preferred embodiments to provide the tampons according to the present invention. But it is understood that the tampons of the present invention are not intended to be limited to those obtainable by the process described herein starting from a tampon blank as described herein. Those skilled in the art would be able to use alternative process features to arrive to the tampons of the present invention having the desired improved expansion characteristics upon exposure to a wet environment.

Figures 3, 4:
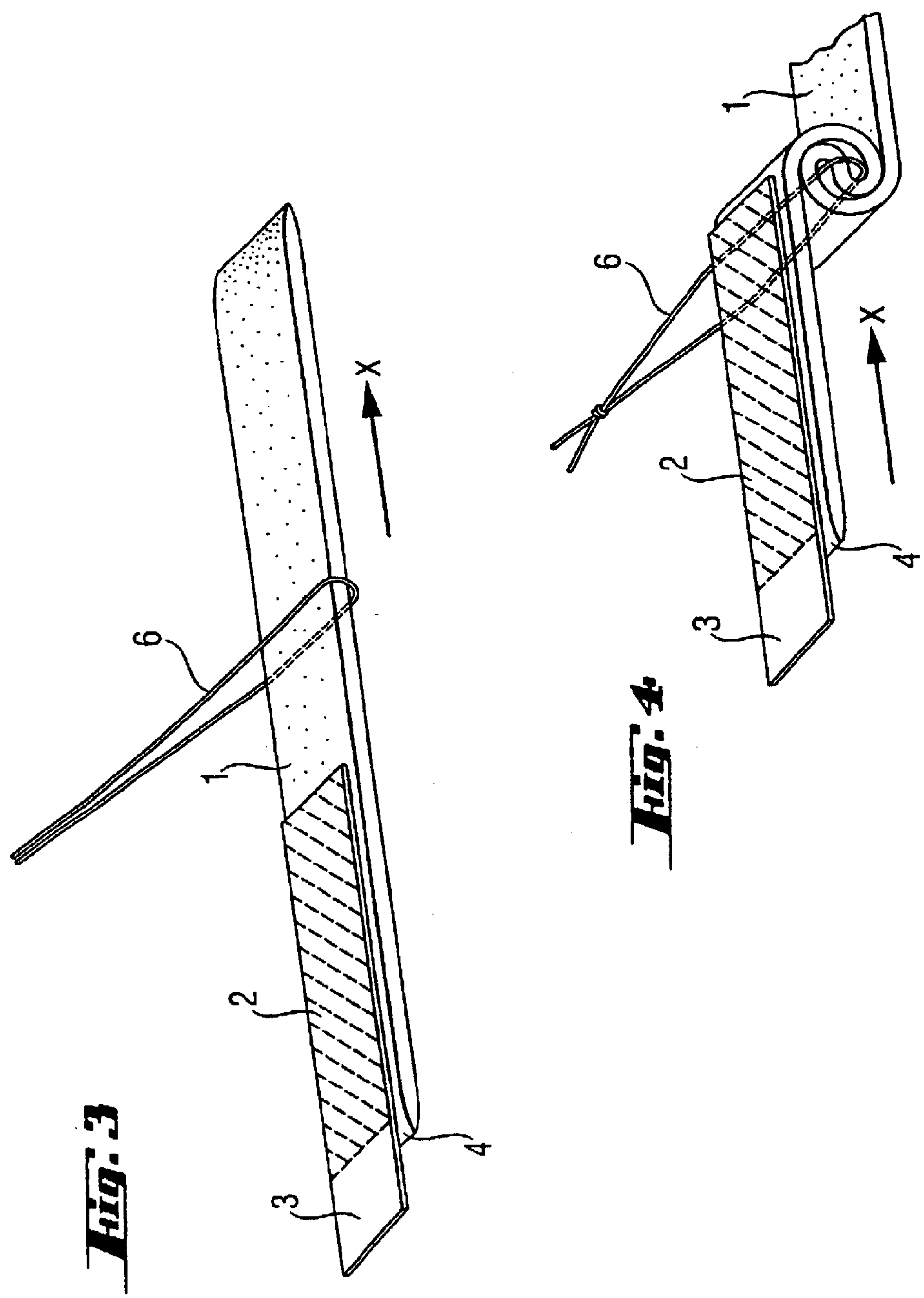

According the FIG. 3, before the winding operation, a retrieval string 6 is typically laid around the nonwoven material 1, transversely to the longitudinal direction of the latter, and if necessary, subsequently knotted at its free end. Thus the tampon 10 is generally provided with a retrieval string 6.

Figure 14:
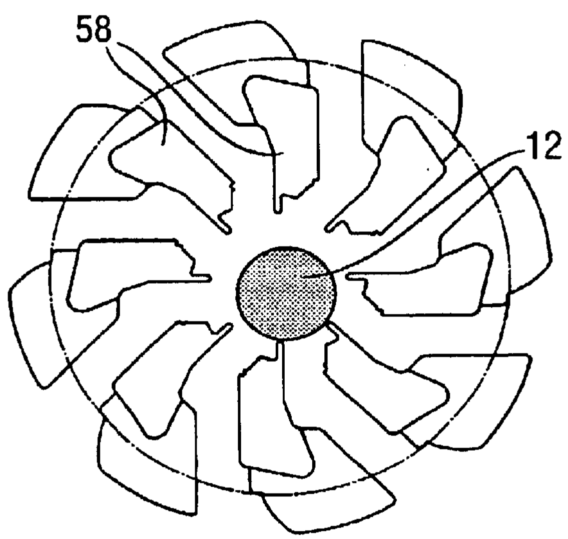
FIG. 14 shows a diagrammatic view of a preforming press 36 in the opened state with a tampon blank arranged in it, offset from the mid axis of the press
Figure 15:
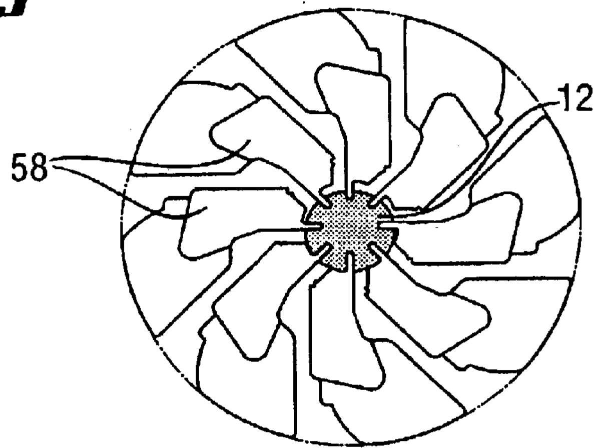
FIG. 15 shows an intermediate closing movement of the press jaws.
Figure 16:
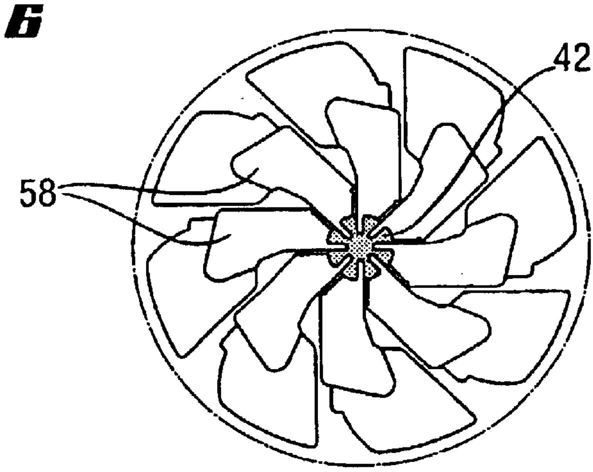
FIG. 16 shows diagrammatic view of a press 36 in the closed state with a tampon blank arranged in it.

The tampon blank 12 which is of a non-circular circumferential shape (preferably elliptically shaped) is then fed to a press, which typically comprises at least 4 identical press jaws arranged in a star shape. The number of jaws can be even or uneven, preferably 6 to 9 and more preferably 7 to 9. Accordingly, the circumferential surface of the tampon blank is pressed radially over at least 4, preferably 6 to 9, and most preferably 7 to 9 portions mutually adjacent in the circumferential direction of the tampon blank into a tampon preform 42 which has a central approximately cylindrical fibre core 62 and longitudinal ribs 64 which extend radially outwards from the fibre core. In a preferred embodiment the tampons herein have an uneven number of ribs, this feature is believed to further participate to the non-circular expansion properties of the tampons herein when exposed to a wet environment and thus such an execution is believed to further reduce by pass leakage. Preferably the circumferential surface of the tampon blank is pressed radially relative to a longitudinal axis which is offset from the mid-axis of the tampon blank. Preferably no centralisation of the tampon blank in the press is done before closing the press. In absence of any centralisation of the tampon blank in the press, the tampon blank while being fed in the press will have the tendency to fall into it so that when the press closes the tampon blank will not be pressed relative to its mid axis but relative to an axis, which axis is offset from the mid axis of the tampon blank. As a result of the tampon blank being pressed radially relative to a longitudinal axis being offset from the mid axis of the tampon blank, the adjacent portions formed (ribs), are non-uniform in the sense of having different widths. Appropriate regulation of the machinery equipment will allow to control/increase this phenomenon. The non-uniformity of the ribs will further contribute to a non-circular expansion during use and thus to an even more appropriate adaptation to the morphology of the vagina and hence a further reduced by pass leakage. This further participates in providing a particular tampon with improved radial expansion properties in use. FIGS. 14 to 16 illustrate this pressing sequence with a tampon blank 12 disposed in the press relative to an axis which is not the mid axis of the press in its open position (FIG. 14).

Thereafter the resulting preform 42 is allowed to expand radially relative to the longitudinal axis of the preform thereby forming the final form of the tampon in such a way that the outer ends 182 of the longitudinal ribs 64 form a soft cylindrical surface of slightly bigger diameter than the diameter of the preform 42. This expansion process which results in a final tampon having a cylindrical surface of bigger diameter than those of the preform further contributes to the expansion feature of the tampon when exposed to a wet environment, thereby further reducing or preventing bypass-leakage in use conditions. The expansion step of the present process confers more conformability and a less dense outer end surface of the ribs of the tampon as opposed to a process wherein after compression of the preform the ribs are exposed to a low uniform pressure radial relative to the longitudinal axis of the preform to result in a tampon with a cylindrical surface of smaller diameter than the diameter of the preform. As a result of the present expansion process the longitudinal ribs have the tendency to touch each other not only at the outer ends 182 but also along almost their entire facing side 183, preferably in a way so that there is no holes between two longitudinal adjacent ribs 64 (see FIG. 12). It is believed that as adjacent ribs touch each others along almost their entire facing side typically without any hole therebetween, an improved cross sectional fluid transport is observed between adjacent ribs. This contributes to a better use of the full absorption capacity of the whole tampon and thus further participates to reduce fluid by pass leakage.

FIG. 12 shows an enlarged cross-sectional representation of the fibre structure of the tampon according to the invention. It is possible to see clearly the central fibre core 62, from which extend outwards the longitudinal ribs 64 touching one another not only at their outer ends 182 but also along most of their facing side 183. The process according to the present invention guarantees a fibre core 62 having a high fibre compression despite the expansion phase after the compression phase. Indeed the digital tampons herein have a stability also called longitudinal crush resistance of at least 15N, preferably at least 20N and more preferably at least 30N. Typically the diameter of the tampon according to the invention is between 8 and 18 mm in its final form.

FIG. 10 illustrates an apparatus for producing a digital tampon 10 according to FIG. 9. It comprises a preforming press 36 having an entry side 38 and an exit side 40 and serves for pressing the tampon blank 12 to obtain a tampon preform 42. The preforming press 36 is equipped with press jaws 58 which are arranged in a plane perpendicular to the press axis A and are movable radially relative to the press axis A. In the closed state of the press jaws 58, the end faces of the latter form an essentially cylindrical, stepped pressing surface, by means of which one of a plurality of directly adjacent sectors S of the entire circumferential surface of a tampon blank is loaded respectively for the purpose of pressing a longitudinal groove 180 and a directly adjacent longitudinal rib 64 (FIG. 11).

The preforming press 36 is preceded by a tube 44 having a pushing means 46. The tube is arranged so as to be movable to and for coaxially relative to the axis of the preforming press 36 and serves for shaping the tampon blank with a circumferencial shape which is non-circular as defined herein before (see FIGS. 7 and 8). The pushing means serves for pushing a respective tampon blank into the opened preforming press 36, the front of the tampon blank being at the front in the pushing-in direction corresponds to the insertion end of the resulting tampon and the rear of the tampon blank being at the end of the pushing-in direction corresponds to the withdrawal end of the resulting tampon.

Figure 20:
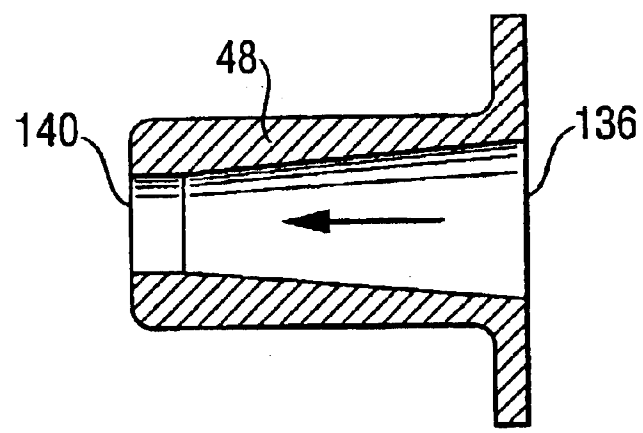
FIG. 20 shows a longitudinal mid-section view of the guiding cone 48 disposed after the preforming press 36 (cf FIG. 10)

The apparatus comprises, further, a guiding cone 48 which allows to guide the preform tampons from the press to the expansion pipe 56. This cone 48 is arranged coaxially relative to the press axis A of the preforming press 36 and is provided with an inlet orifice 136 and an outlet orifice 140. The diameter of the inlet orifice 136 of the cone is always bigger than the diameter of the outlet orifice 140 of the cone 48 (FIG. 20). The outlet orifice 140 of the cone 48 is dimensioned so as to not exercise any pressure on the tampon preform and accordingly is of the same cross sectional diameter or of a bigger cross-sectional diameter than the diameter of the tampon preform coming out of the preforming press 36. This guiding cone as for sole purpose the centralisation of the preform tampon coming out of the press, in the expansion pipe. No radial pressure is exercised on the tampon preform to maintain as much of the oval 'shape memory' of the tampon blank as possible. Any internal shaping of this cone is suitable, e.g, spherical or even quadrangular.

Figure 21:
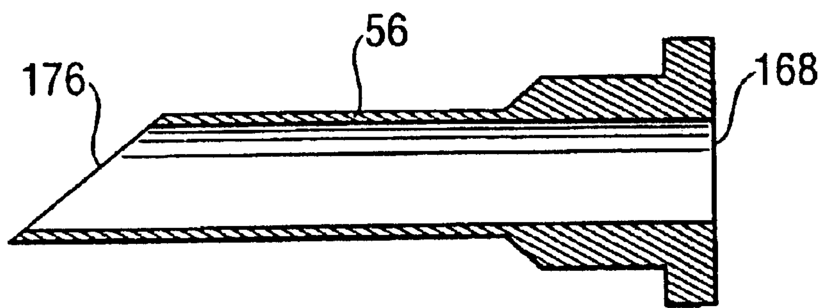
FIG. 21 shows an elevation view of the expansion pipe 56 disposed after the guiding cone 36 in FIG. 10.

The guiding cone 48 is followed by the cylindrical expansion pipe 56 (FIG. 21) with an inlet orifice 168 and an outlet orifice 176. The diameter of the expansion pipe is uniform through its entire length and is bigger than the diameter of the tampon preform coming out of the preforming press. This allows expansion of the preform after the press 36 so that the outer ends of the longitudinal ribs form a soft circumferential surface of bigger diameter. This expansion process further contributes to maintain as much of the oval 'shape memory' of the tampon blank as possible. The cylindrical expansion pipe can have a circular cross-section or a non-circular cross section typically an ellipsoidal cross section. In one embodiment of the present invention this expansion pipe further supports the oval 'shape memory' for the tampon blank by having a non-circular cross-section and preferably an ellipsoidal cross section.

Thereafter the tampon will be pressed co-axially to allow the formation of the tapered tip (machinery not shown in drawings). As a rule, there is an extra machinery equipment provided with a recess, known per se and therefore not shown, which resembles a spherical elongated cup and by means of which the insertion end of the tampon 10 is shaped in the manner of an elongated rounded tip 15. In this case, there is provided in a likewise known way a counter-ram (not shown) which is moved up against the withdrawal end of the tampon 10 at the moment when a first ram is moved up against the insertion end of the tampon 10. Rams/counter-rams of this type are known in the art, and therefore there is no need to represent the driving elements for the rams. Typically the length of the head L is made of at least 50%, preferably more than 55%, more preferably from 60% to 150% and most preferably from 65% to 90% of the diameter D of the tampon (see FIG. 9). This provides elongated shaped insertion end for optimal ease of insertion of the digital tampons of the present invention. D is the diameter of the tampon taken at its middle (i.e., at equal distance from the extremities of both the withdrawal end and the insertion end). L is the length of the head/elongated tip insertion end taken from its extremity up to the point where the diameter of the tampon starts to decrease as compared to the diameter D taken in the middle of the tampon.

Figure 13:
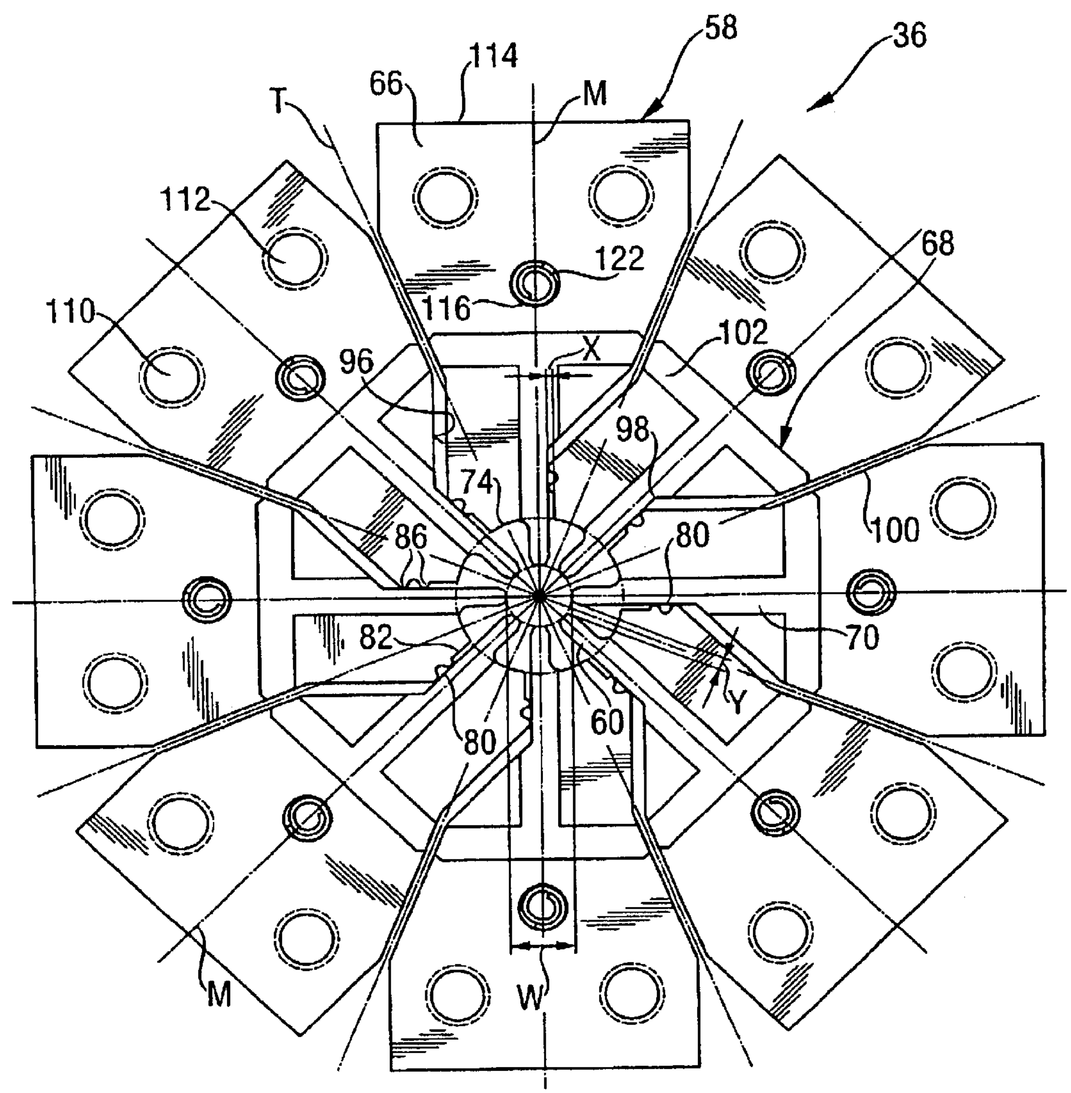
FIG. 13 shows a view of the exit side of a preforming press 36 for the preform, with closed asymmetric press jaws.

The preforming press 36 with eight press jaws 58 is shown on a larger scale in its closed position in FIG. 13. All the press jaws 58 are identical in respect of their shape and dimensions. Furthermore, the press jaws 58 are arranged so as to be movable synchronously into the closed or open position radially and concentrically relative to the press axis A (FIG. 10). It is believed that the tampon blank in the press undergoes an overcompression, so that the circumferential length of the press orifice formed by the closed press jaws 58 is bigger than the circumference of the tampon blank taken at the outer ends of the ribs (see also the cross-section of the preform 42 FIG. 11). The use of 7 to 9 press jaws 58, in conjunction with pressing heads 60 (FIG. 17) of specific dimension, results in the best possible proportion by volume in a central fibre core 62 (FIG. 11) and in the longitudinal ribs 64 of the preform 42 which extend radially from the fibre core 62. However, depending on the desired tampon size, the number of press jaws 58 can also be selected lower or higher. As a result of the simultaneous closing movement of the press jaws 58, a compaction, ensuring the high stability of the digital tampon 10 of a relatively small quantity of the fibre material is obtained coaxially relative to the longitudinal axis being offset from the mid-axis of the tampon preform 42. As a result of the core overpressured process exercised by the pressing heads 60 and offsetting pressure longitudinal towards an axis which is typically not the mid axis of the preform a larger quantity of less compacted fibre material is available and can be activated immediately by fluid coming into contact with it in contrast to the conventional tampon produced by similar process as described typically in EP-A-611 562. Advantageously a greater proportion of the fibre material (ribs) can be activated by the fluid coming into contact with the tampon 10 and can be used for the purpose of fluid absorbency and expansion capacity. Indeed, when wetted with fluid, the tampons of the present invention endeavour to expand to the original, non-circular cross section of the tampon blank and therefore provide improved expansion properties. As a result the risk of bypass leakage is reduced as compared to conventional tampons which expand in a circular shape upon exposure to a wet environment.

This above-described functioning of the press jaw 58 is promoted not only by their synchronous closing and opening movement concentric relative to the press axis A, but also by their special shaping and fastening which are explained in more detail below.

Figure 17:
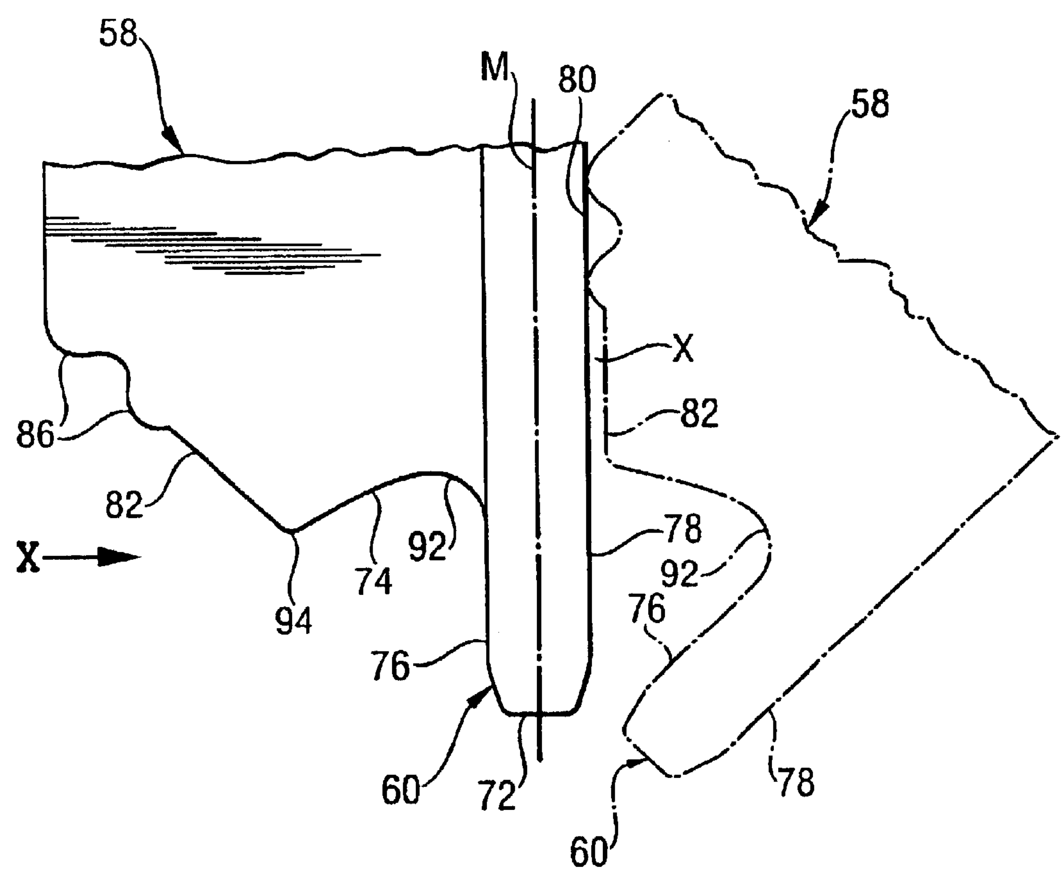
FIG. 17 shows a top view of two press jaws of the preforming press 36 in FIG. 13 located next to one another, in a partially cut-away, enlarged representation
Figure 19:
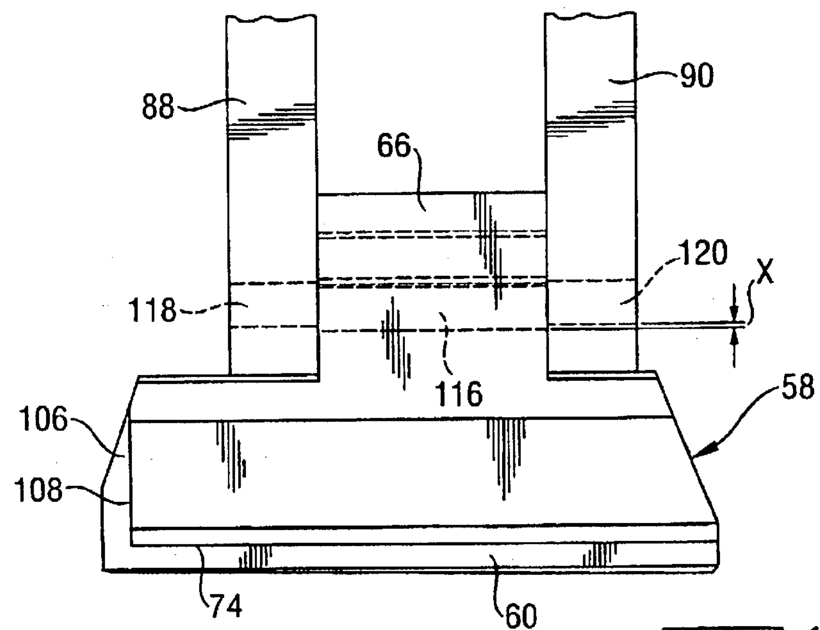
FIG. 19 shows a side view of a press jaw in the direction of the arrow X in FIG. 17 and its fastening to fastening arms of the preforming press.

According to FIGS. 13, 17 and 19, each press jaw 58 has a fastening foot 66 which is fastened radially relative to the press axis A, on guide batons 88, 90 arranged parallel at a distance from one another, by fastening means (not shown), such as screws, and merges radially inwards into a T-profile 68. It is evident that a longitudinal mid-axis M of each press jaw 58, which is directed radially relative to the press axis A, passes through the longitudinal centre of a vertical T-leg 70 of the T-profile 68. The vertical leg 70 of this T-profile 68 forms, at the inner end, a pressing head 60 having a narrow, rectangular and plane end pressing surface 72. In FIG. 13, a pressing shoulder 74 extends from the pressing head 60 transversely relative to this eccentrically in an anti-clockwise direction and is set back radially outwards relative to the pressing surface 72 of the pressing head 60 by an amount corresponding approximately to the radial distance between the outer surface of the longitudinal rib 64 and the outer circumference of a fibre core 62 likewise of circular cross-section. As shown more clearly in FIG. 17, lateral flanks 76, 78 of the pressing head 60 converge in the direction of the pressing surface 72 at a very acute angle of a few minutes over a length corresponding approximately to the distance between the pressing shoulders 74 and the end pressing surface 72 of each pressing head 60. This convergence of the lateral flanks 76, 78 makes it easier for the pressing heads 60 to release the fibre material and for the preform 42 to be pushed out of the opened preforming press 36. The longitudinal edges formed by the pressing surface 72 and by the lateral flanks 76, 78 are rounded.

The press core diameter W is determined in that, on the one hand, the necessary absorbency of the tampon 10 is maintained and, on the other hand, the desired stability is achieved. According to FIGS. 13 and 18, in the closed state of the preforming press 36, the smallest lateral distance Y between adjacent pressing jaws 58 is defined in that, during pressing, no fibre material 84 is cut and the preform 42 maintains the necessary shape. As emerges more clearly from FIG. 18, for this purpose there is an interspace X which, furthermore, is intended to prevent the tampon 10 from being pushed out. The interspace X, the width of which amounts, for example, to 0.45 mm, is limited respectively by mutually opposite longitudinal sides of adjacent press jaws 58. At the same time, a longitudinal side of each press jaw 58, said longitudinal side being at the front in the clockwise direction, forms a sliding face 80, opposite which a longitudinal side, at the rear in the clockwise direction, of a press jaw 58 arranged respectively in front in the clockwise direction is located, parallel and at a distance, in the form of a supporting face 82. This interspace X allows the fibre material 84 to be taken up by the lateral flank 78 of each press jaw 58 located at the front in the clockwise direction, in such a way that a fin formation on the outside of the longitudinal rib 64 of the preform 58 is avoided and a smooth, round outer face between the lateral flank 78 and the adjoining sliding face 80 of each press jaw 58, on the one hand, and the supporting face 82 of a press jaw 58 arranged in front in the clockwise direction, on the other hand, is obtained.

Furthermore, it can be seen clearly from FIG. 17 that the interspace X between the adjacent press jaws 58 is closed radially outwards by supporting ribs 86 which have, in cross-section, an arcuate, for example U-shaped, profile and which, in the closed state of the press jaws 58, are supported on the plane sliding face 80 of the respective adjacent press jaw 58.Lateral forces acting on each press jaw 58 are thereby not transmitted to the guide batons 88, 90 for the press jaws 58 (FIG. 19). The accumulation of fibre material 84 and its occasional settling on the preform 42 are thereby prevented.

Figure 18:
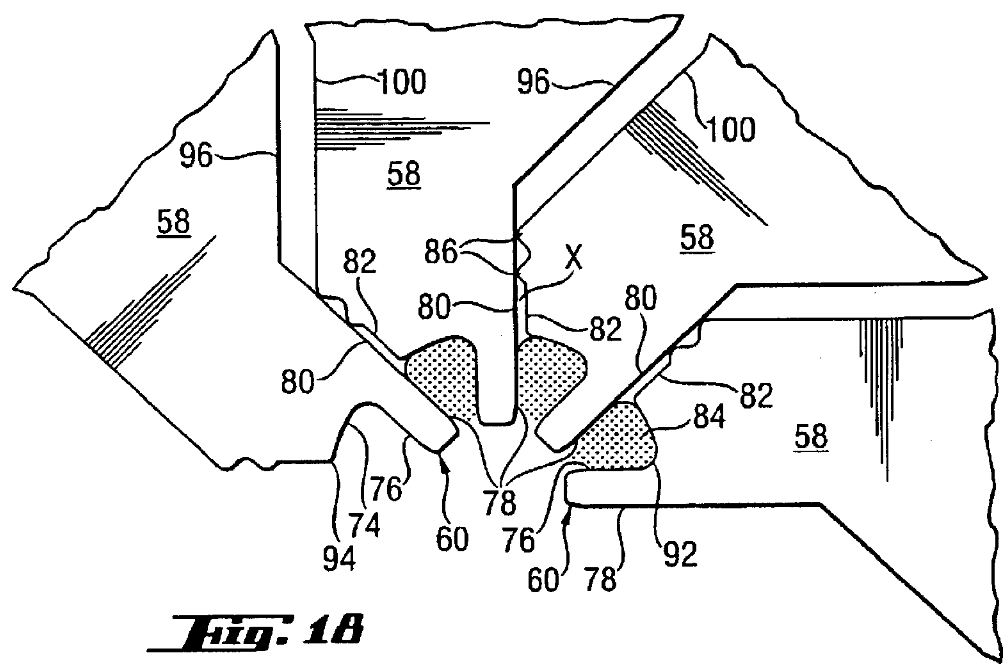
FIG. 18 shows a view of a plurality of press jaws in the closed state, which illustrates the influence of an interspace on one side of each press jaw on the fibre material of the preform

FIGS. 17 and 18 show that a pressing-shoulder portion 92 in the form of a cylindrical cutout connects the actual pressing shoulder 74 to the lateral flank 76 of each pressing head 60, in order to give the longitudinal rib 64 of the preform 42 a round, smooth shape also on the side facing away from the interspace X. The pressing shoulders 74 of all the press jaws 58 have a concave shape and, for example, a radius of curvature of approximately 6.4 mm.

FIG. 13 illustrates that the radial parting planes or planes of symmetry T, parallel to the press axis A, between respective adjacent press jaws 58 intersect the press shoulders 74 perpendicularly at their centre and respectively form the centre of the press-jaw distance Y. An end of each pressing shoulder 74 located in the anti-clockwise direction in FIG. 17 forms a shoulder edge 94 which merges at an obtuse angle into the supporting face 82 of each associated press jaw 58. The supporting face 82 of each press jaw 58 extends parallel to the sliding face 80 and longitudinal mid-axis M of the respective press jaw 58 adjacent in the anti-clockwise direction and engages respectively into a lateral cutout 96 of this press jaw 58. This cutout 96, which is accordingly provided respectively on the side of each press jaw 58 located at the front in the clockwise direction, is partially cut into the vertical T-leg 70, extending along the longitudinal mid-axis M of each press jaw 58, of each press jaw 58, in the form of the sliding face 80 parallel to this longitudinal mid-axis. This sliding face 80 is angled at 98 at an obtuse angle in the clockwise direction at its end on the outside in relation to the associated pressing head 60 and is located, in parallel and at a distance, opposite a face 100 of the respective press jaw 58 located at the front in the clockwise direction. Thereafter, these faces 80, 100 located opposite one another in parallel and at a distance are angled relative to one another in parallel and at a distance in the direction of the parting plane T in the region of the outer ends of horizontal T-profile bars 102 and fastening feet 66 of the press jaws 58. It is thus evident that the pressing shoulder 74 of each press jaw 58 engages beyond the associated parting plane T into the cutout 96 of the adjacent press jaw 58 and allows the asymmetric or one-sided arrangement of the press shoulder 74, for the purpose of pressing the fibre material of the tampon blank inwards from the outside, while avoiding any fin formation, and of shaping the essentially cylindrical outer contour of the preform 42.

According to FIG. 19, the pressing head 60 of each press jaw 58 projects, with its side 106 facing the guiding cone 48, beyond an associated end 108 of the pressing shoulder 74, the function of said end 108 being explained further below. Furthermore, the fastening foot 66 of each press jaw 58 has two rear fastening bores 110, 112 (FIG. 13) which are arranged at an equal distance from the longitudinal mid-axis M of each press jaw 58 in a plane parallel to a rear edge 114 of the fastening foot 66. Located on the longitudinal mid-axis M of each press jaw 58, at a distance in front of the plane running through the fastening bores 110, 112, is a further bore 116 which extends through the fastening foot 66 in parallel with the fastening bores 110, 112. The guide batons 88, 90 are each provided with three bores which are located coaxially opposite one another in pairs and which are aligned essentially with the fastening bores 110, 112, 116 in the fastening foot 66 of each press jaw 58. In this way, the press jaws 58 can be releasably fastened, for example by means of screws (not shown), respectively to the two guide batons 88, 90 assigned to them, parallel and at a distance and arranged in the direction of the longitudinal mid-axis M of the press jaws 58, and be moved radially to and fro.

FIG. 19 shows only two coaxial bores 118, 120 in the guide batons 88, 90, which are assigned to the bore 116 in the fastening foot 66 of each press jaw 58. However, the bore 116 in the fastening foot 66 is offset axially by an amount "X" in the direction of the pressing heads 60 relative to the bores 118, 120 of the guide batons 88, 90. A helical tension pin 122 is inserted, according to FIG. 13, into the bores 116, 118, 120 of each of the press jaws 58. This helical tension pin 122 extends over the entire length of the bores 116, 118, 120 and thereby ensures an identical setting-up state of all the press jaws 58. In addition to this dimensional equality, the helical tension pins 122 at the same time allow a resilient compensation against possible lateral transverse forces which act on the press jaws 58. In the closed state of the preforming press 36, under working pressure, an identical and centric closing diameter of the press jaw 58 is always achieved thereby, this contributing to ensuring a high fatigue strength of the preforming press 36 and a constant high quality of the tampon as a mass-produced product.

The production of the tampon according to the invention by means of the above-described apparatus is carried out according to the following process: Once the non-circular tampon blank 12 has been fed in the press 36 narrow rib-shaped or strip-shaped sectors of the circumferential surface of the tampon blank, which are parallel relative to the press axis A and which are separated from one another by non equal circumferential angles as a result of the radial pressure of the press jaws 58 relative to an axis being offset from the mid axis of the tampon blank, are pressed radially relative to the press axis A as a result of the synchronous concentric closing movement of the press jaws 58, and the longitudinal grooves 180 are formed.

Simultaneously, by means of the pressing shoulders 74 of the same press jaws 58, which are located respectively on that side of the associated pressing head 60 directed in the anti-clockwise direction according to FIG. 13, larger portions of the same sectors of the circumferential surface of the tampon blank are subjected to a pressing force to form the longitudinal ribs 64. Consequently, the preform 42 is obtained in one work cycle of the press jaws 58 moving jointly into the closed position. During the forming of the longitudinal grooves 180, the central fibre core 62 is produced, whilst the longitudinal ribs 64 extend radially outwards laterally of the longitudinal grooves 180.

After the preform 42 has been pressed, it is guided via the guiding cone 48 into the expansion pipe 56 where it expands in the final shape of the tampon with a diameter being at least slightly bigger than the diameter of the preform 42 coming out of the preforming press 36. Thereafter the tapered tip is formed. Two rams thereby exert an oppositely directed axial pressure on the tampon 10 which is consequently provided with the rounded elongated tip 15 for the insertion end 17 of the tampon 10 and with the finger recess for the withdrawal end 18 of the tampon.

In a particular embodiment herein, the press jaws 58 and in particular the pressing shoulder 74 could be adapted so that they ensure that at least the fibre material located in the region of the withdrawal end of the tampon 10 has an overall lower compaction than the remaining fibre material of the tampon. Consequently, the retrieval string 6 of the tampon 10 can be embedded into a less compacted fibre material at the withdrawal end of the tampon 10 and can more easily be detached by hand from this fibre composite, with a finger recess thereby being formed or widened/flared. In addition, a higher speed or expansion of the fibre material, which counteracts a leakage shortly after starting to use the tampon, is achieved in the region of the withdrawal end of the tampon.

In the above-described process for producing the tampon 10, it is also possible, if appropriate, to bring about the lower compression of the fibre material at the withdrawal end by means of the pressing surface, offset in a step-like manner, of the pressing heads 60. Moreover, it would be possible, if appropriate, to press the longitudinal grooves of the preform 42, starting at its front or insertion end, over its entire length to an increasingly lesser extent in the direction of the withdrawal end.

EXAMPLE

A series of fibrous webs were formed by mixing multi-limbed regenerated cellulosic staple fibers (Galaxy® fibers, 3.3 denier, rayon fibers available from Acordis, England) and non-limbed fibers (Danufil® fibers, 3.6 denier, rayon fibers available from Hoechst Kehlheim, Germany) at a fiber ratio of Galaxy®:Danufil® of 70:30. The resulting blend was carded to obtain fibrous webs. These webs were then used to manufacture compressed radially-expanding tampons according to the present invention starting from tampon blanks having an ovality coefficient (OC(tampon blank)) as defined herein of 13. The tampons obtained have 8 ribs.

The minor and major diameters at the middle of tampon samples to be tested (i.e., taken at equal distance from both the extremity of the withdrawal end and the extremity of the insertion end) were measured before (on the so called tampon) and after exposure to the EDANA syngina method (on the so called expanded tampon). The minor diameter was defined as the narrowest diameter of the tampon/expanded tampon. The major diameter was measured by a 90° turn of the tampon/expanded tampon after the minor diameter was identified and measured. These diameters were measured with a Tampon Gauge (with a calliper that is accurate to 0.1 mm), namely a Mitutuyo Digimatic Scale Unit #572-213, 0–300 mm. Table 1 herein after reports the major and minor diameter values for the middle of the tampon samples tested and corresponding expanded tampons (i.e., at the end point of the EDANA syngina method), the weight of the tampon samples to nearest 0.01 g before exposure to the syngina method, the absorption capacity of the tampon samples measured by the syngina method and the ovality coefficient defined at the end point of the syngina method. To do the measurements of the minor and major diameters on the expanded tampon samples (i.e., after exposure to the syngina method) care was taken to not squeeze the tampons.

The tampon samples were exposed to the EDANA syngina method according to 'EDANA agreed test method 350.0-99'. This test was strictly followed. The end point of the EDANA syngina method was defined by the first drop of syngina liquid that exits the syngina apparatus. The syngina fluid used is a sodium chloride solution as defined in the EDANA syngina method with colorant FD&C #40 (from Phylam products Co). The condoms used a Durex tampon No X2111T thin Starch. The condoms were stored in a closed container until used.

Table 1 herein after gives details of the results obtained on 16 tampon samples. From these data it can be seen that the tampons of the present invention expand under wet conditions in a non circular cross-sectional shape, typically in an ellipsoidal shape. Advantageously these tampons have been found to reduce the occurrence of bypass leakage during use.

TABLE 1

| Units | TAMPON WEIGHT GRAMS | TAMPON MAJOR DIAMETER MM | TAMPON MINOR DIAMETER MM | EXPANDED TAMPON MAJOR DIAMETER MM | EXPANDED TAMPON MINOR DIAMETER MM | EXPANDED TAMPON OVALITY COEFFICIENT (%) | ABSORBENCY GRAMS |
|---|---|---|---|---|---|---|---|
| test | 2.18 | 12.64 | 12.42 | 22.7 | 19.59 | 15.88 | 9.99 |
| samples | 2.15 | 12.71 | 12.47 | 21.33 | 19.84 | 7.51 | 10.73 |
| | 2.29 | 12.77 | 12.6 | 22.23 | 18.95 | 17.31 | 11.25 |
| | 2.22 | 12.54 | 12.41 | 22.94 | 19.74 | 16.21 | 9.93 |
| | 2.2 | 12.64 | 12.5 | 21.82 | 18.48 | 18.07 | 9.43 |
| | 2.3 | 12.75 | 12.54 | 22.76 | 19.24 | 18.30 | 11.39 |
| | 2.3 | 12.65 | 12.5 | 21.67 | 19.1 | 13.46 | 10.81 |
| | 2.13 | 12.78 | 12.52 | 21.8 | 18.12 | 20.31 | 10.4 |
| | 2.14 | 12.64 | 12.5 | 22.29 | 18.39 | 21.21 | 10.18 |
| | 2.13 | 12.63 | 12.45 | 21.85 | 18.2 | 20.05 | 9.64 |
| | 2.16 | 12.53 | 12.5 | 22.5 | 18.51 | 21.56 | 10.36 |
| | 2.35 | 12.51 | 12.44 | 23.37 | 19.84 | 17.79 | 11.4 |
| | 2.27 | 12.85 | 12.48 | 22.75 | 18.38 | 23.78 | 10.52 |
| | 2.24 | 12.7 | 12.49 | 21.39 | 18.84 | 13.54 | 11.3 |
| | 2.2 | 12.62 | 12.3 | 21.26 | 18.55 | 14.61 | 10.74 |
| | 2.28 | 12.71 | 12.45 | 23.07 | 18.83 | 22.52 | 10.99 |
| Average | 2.22 | 12.67 | 12.47 | 22.23 | 18.91 | 17.63 | 10.57 |
| Std.Dev. | 0.07 | 0.10 | 0.07 | 0.67 | 0.59 | 4.04 | 0.62 |
| N | 16 | 16 | 16 | 16 | 16 | 16 | 16 |

What is claimed is:

1. A digital vaginal tampon comprising a substantially cylindrical mass of compressed fibers having an insertion end and a withdrawal end, the insertion end having an elongated tip shaped insertion end/head wherein the length of the head L is at least 50% of the diameter of D of the tampon, the tampon being capable of radially expanding into a non-circular shape upon exposure to a wet environment, so that the ovality coefficient of the tampon measured at the end point of the EDANA syngina method, referred to as OC (expanded tampon), is from more than about 10 to about 40.

2. A tampon according to claim 1 wherein OC (expanded tampon) is from about 13 to about 40, more preferably from about 15 to about 40, even more preferably from 18 to about 30, and most preferably from about 20 to about 28.

3. A tampon according to claim 1 wherein the tampon comprises a fluid-permeable covering material such that the cylindrical mass of compressed fibers is substantially enclosed by such a covering material.

4. A tampon according to claim 3 wherein said covering material is a nonwoven covering material which is at least partly composed of thermoplastic fibers.

5. A tampon according to claim 1 wherein the compressed fibers are composed of non-limbed cellulosic fibers, regenerated cellulosic fibers having multi-limbed cross section or mixture thereof.

6. A tampon according to claim 1 wherein the tampon is composed of a core surrounded by at least 4 ribs, preferably at least 6 and more preferably from 7 to 9 which extend radially outwards from the core, wherein adjacent ribs touch each other not only at their outer end to form a soft cylindrical surface but also along almost their entire facing side.

7. A tampon according to claim 1 wherein the tampon is composed of a core surrounded by at least 4 ribs, preferably at least 6 and more preferably from 7 to 9 which extend radially outwards from the core, said ribs being non-uniform.

8. A tampon blank obtainable by winding essentially upon itself a portion of length of nonwoven material which has a width approximately corresponding to the length of the tampon, preferably in presence of a fluid permeable covering material, characterized in that the ovality coefficient of the tampon blank, referred to as OC (tampon blank), is from more than 10 to 45.

9. A tampon blank according to claim 8 wherein OC (tampon blank) is from about 15 to about 45, more preferably from about 18 to about 45, even more preferably from about 20 to about 40, and most preferably from about 22 to about 35.

10. A process for producing digital tampon according to any of the claim 1, in which a tampon blank according to claim 8 is shaped by winding up a nonwoven material, preferably in presence of a fluid permeable covering material, the tampon blank is then pressed radially to form a tampon having a central approximately cylindrical fibre core and longitudinal ribs which extend radially outwards from the fiber core.

11. A process according to claim 10 wherein the tampon blank is pressed radially relative to a longitudinal axis, which axis is offset from the mid-axis of the tampon blank over at least 4 portions mutually adjacent in the circumferential surface of the tampon blank, preferably at least 6 and more preferably from 7 to 9 portions.

12. A process according to claim 10 wherein the tampon after having been radially pressed is left to expand, typically in an expansion pipe, in its final shape so that the outer end of the longitudinal ribs form a soft cylindrical surface of at least slightly bigger diameter.

13. A process according to claim 10 wherein the tampon is provided with an elongated tip shaped insertion end by exercising an oppositely directed axial pressure on the insertion and withdrawal ends.

* * * * *